US012594036B2

(12) United States Patent
Fabregat Sanjuan et al.

(10) Patent No.: US 12,594,036 B2
(45) Date of Patent: Apr. 7, 2026

(54) METHOD AND SYSTEM FOR GUIDING ELECTRODE PLACEMENT ON THE SCALP

(71) Applicants: UNIVERSITAT ROVIRA I VIRGILI, Tarragona (ES); INSTITUT D'INVESTIGACIÓ SANITÀRIA PERE VIRGILI, Tarragona (ES)

(72) Inventors: Albert Fabregat Sanjuan, Tarragona (ES); Vicenç Pascual Rubió, Tarragona (ES)

(73) Assignees: UNIVERSITAT ROVIRA I VIRGILI, Tarragona (ES); INSTITUT D'INVESTIGACIÓ SANITÀRIA PERE VIRGILI, Tarragona (ES)

( * ) Notice: Subject to any disclaimer, the term of this patent is extended or adjusted under 35 U.S.C. 154(b) by 272 days.

(21) Appl. No.: 18/290,187

(22) PCT Filed: May 9, 2022

(86) PCT No.: PCT/EP2022/062451
§ 371 (c)(1),
(2) Date: Nov. 10, 2023

(87) PCT Pub. No.: WO2022/238311
PCT Pub. Date: Nov. 17, 2022

(65) Prior Publication Data
US 2024/0252112 A1     Aug. 1, 2024

(30) Foreign Application Priority Data

May 11, 2021     (EP) ..................................... 21382429

(51) Int. Cl.
*A61B 5/00*          (2006.01)
*G01B 7/14*          (2006.01)

(52) U.S. Cl.
CPC ............ *A61B 5/6841* (2013.01); *A61B 5/742* (2013.01); *A61B 5/748* (2013.01); *G01B 7/14* (2013.01)

(58) Field of Classification Search
None
See application file for complete search history.

(56) References Cited

U.S. PATENT DOCUMENTS 3,998,213 A * 12/1976 Price ...................... A61B 5/276
                                                              600/383
5,293,867 A * 3/1994 Oommen ............. A61B 5/6841
                                                              600/383
(Continued)

FOREIGN PATENT DOCUMENTS

AU          2017202427 A1     5/2017
CN          108523886 A       9/2018
(Continued)

OTHER PUBLICATIONS

Beam, William, et al., "An efficient and accurate new method for locating the F3 position for prefrontal TMS applications", Brain Stimulation, 2009, pp. 50-54, vol. 2.

*Primary Examiner* — Richard Isla
(74) *Attorney, Agent, or Firm* — The Webb Law Firm

(57)          ABSTRACT

A method and system for guiding electrode placement on the scalp. The invention includes a touch sensor arranged along a section of a flexible LED strip configured for measuring a distance between surface landmarks of the skull; and a control module with different configured settings of electrode placement schemes. By locating different cranial landmarks marked with the touch sensor and confirmed with LED lighting, it allows to guide the precise location of each electrode by illuminating the corresponding points of the LED strip.

19 Claims, 15 Drawing Sheets

(56) References Cited

U.S. PATENT DOCUMENTS

| | | | | |
|---|---|---|---|---|
| 5,518,007 | A * | 5/1996 | Becker | A61B 5/291 |
| | | | | 600/587 |
| 6,175,753 | B1 | 1/2001 | Menkes et al. | |
| 6,510,340 | B1 * | 1/2003 | Jordan | A61B 5/4076 |
| | | | | 600/386 |
| 6,640,122 | B2 | 10/2003 | Manoli et al. | |
| 7,551,952 | B2 | 6/2009 | Gevins et al. | |
| 8,103,328 | B2 * | 1/2012 | Turner | A61B 5/291 |
| | | | | 600/587 |
| 8,538,502 | B1 | 9/2013 | Wilson et al. | |
| 8,577,440 | B2 * | 11/2013 | Afanasewicz | A61B 5/296 |
| | | | | 600/383 |
| 8,731,633 | B2 | 5/2014 | Asjes et al. | |
| 9,579,062 | B2 | 2/2017 | Albert | |
| 10,368,781 | B2 * | 8/2019 | Shifflett | G01B 3/10 |
| 2005/0197556 | A1 * | 9/2005 | Stoler | A61B 5/369 |
| | | | | 600/383 |
| 2007/0238945 | A1 * | 10/2007 | Delic | A61B 5/165 |
| | | | | 600/383 |
| 2011/0015503 | A1 | 1/2011 | Joffe et al. | |
| 2015/0174418 | A1 | 6/2015 | Tyler et al. | |
| 2015/0282709 | A1 * | 10/2015 | Motoyoshi | A61N 1/37223 |
| | | | | 600/545 |
| 2017/0172444 | A1 * | 6/2017 | Brewer | A61B 5/6841 |
| 2017/0258353 | A1 * | 9/2017 | Jovanovic | A61B 5/6831 |
| 2018/0153470 | A1 | 6/2018 | Gunasekar et al. | |
| 2018/0289272 | A1 * | 10/2018 | McCoy | G16H 40/63 |
| 2020/0305795 | A1 * | 10/2020 | Floyd | A61B 5/6814 |
| 2024/0415464 | A1 * | 12/2024 | Noda | A61B 5/7267 |

FOREIGN PATENT DOCUMENTS

| | | |
|---|---|---|
| CN | 111743536 A | 10/2020 |
| EP | 2967407 B1 | 5/2018 |
| GB | 2499595 A | 8/2013 |
| WO | 2007138598 A3 | 12/2007 |
| WO | 2014158803 A1 | 10/2014 |

* cited by examiner

B

46    Start cranial perimeter measurement

47    Hold the start of the strip in Fpz and touch in Oz to measure

48    Is the led on Oz, ok?    Yes    No

49    The cranial perimeter is xx mm (result from measurement x 2)

Mark the illuminated points needed (Fp1/Fp2, F7/F8, T3/T4, T5/T6, O1/O2)

50    Finished!

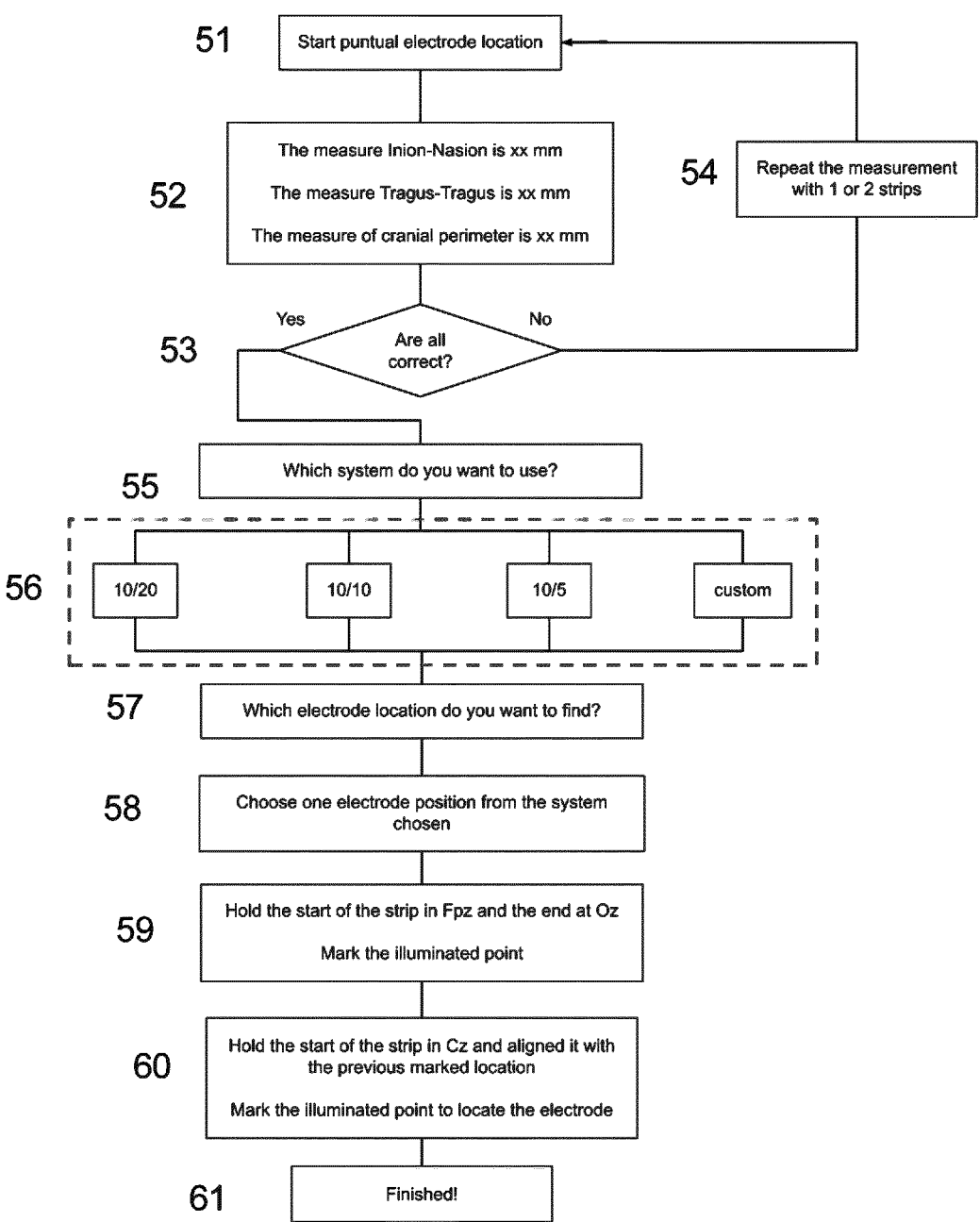

51 — Start puntual electrode location

52 — The measure Inion-Nasion is xx mm

The measure Tragus-Tragus is xx mm

The measure of cranial perimeter is xx mm

54 — Repeat the measurement with 1 or 2 strips

53 — Are all correct?    Yes    No

55 — Which system do you want to use?

56 — 10/20    10/10    10/5    custom

57 — Which electrode location do you want to find?

58 — Choose one electrode position from the system chosen

59 — Hold the start of the strip in Fpz and the end at Oz

Mark the illuminated point

60 — Hold the start of the strip in Cz and aligned it with the previous marked location Mark the illuminated point to locate the electrode 61 — Finished!

FIG.8D

METHOD AND SYSTEM FOR GUIDING ELECTRODE PLACEMENT ON THE SCALP

CROSS-REFERENCE TO RELATED APPLICATIONS

This application is the United States national phase of International Application No. PCT/EP2022/062451 filed May 9, 2022, and claims priority to European Patent Application No. 21382429.5 filed May 11, 2021, the disclosures of which are hereby incorporated by reference in their entireties.

BACKGROUND OF THE INVENTION

Field of the Invention

Present invention relates to the field of test equipment and methods for assisting the placement of electrodes on the scalp.

An object of present invention is to identify specific locations on cranial surface useful for electrode placement and other treatment purposes.

Description of Related Art

In various electrophysiological clinical tests such as evoked potentials, integrated amplitude electroencephalography (aEEG) or polysomnography, it is required to place electrodes at the level of the scalp at certain locations. These locations follow a percentage pattern called the international 10-20 system, because it works by dividing the cranial surface into 10% and 20% segments to locate the underlying the cortical areas of interest. Each individual has a specific cephalic size that varies greatly depending on age so an individualized calculation is required for the placement of these electrodes.

For this reason, a measure tape is typically used, which is placed considering basic anatomical references of the head, and a calculation of the distance is made to determine the different location of the electrodes. Sometimes this calculation is performed in stressful situations by health personnel, such as during a night guard in an intensive care unit with a high care load which causes the relevant measurement and calculations not to be performed accurately.

During intraoperative neurophysiological monitoring (INM) high speed and refined specificity is required for placing electrodes. It is necessary to be very fast because the whole surgical team is usually waiting to start surgeries that are usually long-lasting. In addition, it is necessary to be very precise at the same time to place the electrodes because they usually are intradermal spiral needle electrodes (corkscrew electrodes) that are kept in place during all the surgery time. The relocation of the electrodes is avoided because it usually involves stopping the surgery and endangering the sterilization conditions of the surgical field.

Prior art offers some related systems for placing or assisting to place the electrodes as U.S. Pat. No. 8,731, 633B2, US2017/0172444A1, U.S. Pat. No. 6,175,753B1, AU 2017202427B2, EP2967407, GB2499595, U.S. Pat. No. 6,640,122B2, U.S. Pat. No. 7,551,952B2, U.S. Pat. No. 8,538,502 B1, U.S. Pat. No. 9,579,062B2 or US2011/0015503A1. Actually, none of them are applicable in most hospitals for being complex and expensive. Moreover, existing devices such as helmets or systems based on the fixed determination of the cranial perimeter cannot be used in the operating room because on many occasions it is necessary to take measurements with cranial stabilization systems, such as the Mayfield device. Other problem of prior art structures such as helmets to locate certain cranial points would be the presence of sensors of intracranial pressure, epicranial vein accesses or ventricular drainage devices that occupy part of the scalp.

In short, many devices have attempted to assist the electrode placement on the scalp but they are not used in the majority of real medical situations because they are inaccurate or they are not practical. For example, documents CN 111743536 A and CN 108523886 use the cranial perimeter to locate the electrodes. However, if only the cranial perimeter is used a simplification of the head shape is done because the relation between Inion-Nasion and Tragus (left preauricular point (LPA))—Tragus (right preauricular point (RPA)) dimensions is inaccurately considered fixed. Another example is the document US 20180153470 A1 which comprises a helmet that does not totally adapt to the head (due to the lack of flexibility) and five bands are required in order to totally measure the cranial shape and to locate the majority of the electrodes required in standard neurophysiological tests dimensions.

For all the reasons above, prior art is missing a flexible solution for quickly and accurately guiding electrode placement on the scalp which is suitable for each test performed in the electrophysiology laboratory or in the operating room.

SUMMARY OF THE INVENTION

The present invention solves the aforementioned problems by providing a quick and easy way to determine the placement of the electrodes in the context of different test or studies. A first aspect refers to a system for guiding electrode placement on a scalp comprising:

a first strip arrangement comprising:
    a first flexible LED strip.
    a first touch sensor means arranged along a section of the first flexible LED strip configured for measuring a distance between cranial landmarks; and
a control module connected to the first strip wherein, the control module is configured for setting a first cranial landmark (e.g. right Tragus) at one end of the first flexible LED strip and setting a second cranial landmark (e.g. left Tragus) while activating the touch sensor and illuminating it to check the point selection. Then there is an illumination of the flexible LED strip points for guiding electrode placement, based on the distance between the two basic cranial landmarks and an electrode placement scheme previously set.

In one embodiment of the invention, the system further comprises:

a second strip arrangement connected to the control module, the second strip arrangement comprising:
    a second flexible LED strip;
    a second touch sensor means arranged along a section of the second flexible LED strip; and
a joint element configured for joining the first and the second strip arrangements in a cross shape, wherein the joint element allows relative perpendicular movement between them to align a central position of both strip arrangements;

wherein the control module is further configured for setting a first cranial landmark at one end of the second strip arrangement (e.g. Nasion), setting a second additional cranial landmark (e.g. Inion) where a physical touch is detected by the second touch sensor means and illuminating the second flexible LED strip at least at one location for guiding electrode placement, based on the distance between the two additional cranial landmarks and the electrode placement scheme previously set.

Advantageously, present invention allows locating different cranial landmarks by pressing the touch sensor and confirming them through LED lighting, so that it allows guiding the precise location of each electrode by illuminating the corresponding points of the LED strip following an established color code.

Optionally, according to one embodiment of the invention, the control module is further configured for illuminating the first flexible LED strip at one location signaling a central head reference point. Thus, advantageously, subsequent placement of the same or a second strip is improved.

In one embodiment of the invention the touch sensor means are a soft membrane potentiometer configured for measuring distance between cranial landmarks selected from Inion, Nasion and Tragus. Specifically, in one particular embodiment, the touch sensor means are arranged on a last section of the flexible LED strip and wherein the length of the touch sensor means is selected within a range of 10-20 cm.

Additionally, one embodiment of the invention comprises holding means arranged at one end of the strip arrangement, the holding means are configured for pivot holding the strip arrangement to a patient. In one particular embodiment of the invention, the holding means comprise an adhesive with a snap connector comprising a set of male and female matching connectors, wherein the female connector is adhered to the end of the strip arrangement and the male connector can be adhered to the patient at a cranial landmark (e.g. Nasion or Tragus (equivalent to preauricular point)).

Optionally, the second strip arrangement may comprise additional holding means configured for pivot holding the second strip arrangement to a patient. The additional holding means may comprise ear holding means, chin holding means and/or neck holding means.

Optionally, one embodiment of the invention comprises a glass-shape holder at one end of the first strip arrangement, the glass-shape holder is configured for holding the first strip arrangement to a patient's nose at Nasion cranial landmark.

In one embodiment of present invention, the flexible LED strip comprises two parallel rows of LEDs and a central slot arranged between said two parallel rows of LEDs along a second section different from the section of the touch sensor means. Thus, advantageously, the central slot allows an easy marking of the location by the medical staff without moving the strip.

A second aspect of the invention refers to a method for guiding electrode placement on a scalp characterized by comprising the following steps:

placing a first strip arrangement over the head of a patient, wherein the first strip arrangement comprises a first touch sensor means arranged along a section of a first flexible LED strip;

adjusting one end of the first strip arrangement at a first cranial landmark;

pressing the first strip arrangement on the first touch sensor section at a second cranial landmark;

measuring, by the first touch sensor means, the distance between the two cranial landmarks;

determining, by a control module connected to the first strip arrangement, at least one location along the first strip arrangement for electrode placement, based on the measured distance and an electrode placement scheme previously set; and illuminating the first flexible LED strip at the location for guiding electrode placement.

According to one embodiment of the invention, the method further comprises:

placing a second strip arrangement over the head of the patient, wherein the second strip arrangement comprises a second touch sensor means arranged along a second flexible LED strip and pivot holding means;

holding an end of the second strip arrangement at a lateral cranial landmark of the patient;

pivoting the second strip arrangement until aligning with illuminated locations of the first flexible LED strip pressing the second strip touch sensor means at a contralateral cranial landmark;

measuring, by the second touch sensor means, the distance from the end of the second strip arrangement held to the lateral cranial landmark to the contralateral cranial landmark;

determining, by the control module, at least one location along the second strip arrangement for electrode placement, based on the measured distance and the electrode placement scheme; and illuminating the second flexible LED strip at determined locations for guiding electrode placement.

According to one particular embodiment of the invention, placing the first strip arrangement over the head of the patient comprises placing the first strip arrangement along a line covering Inion and Nasion cranial landmarks; and wherein pressing the first strip arrangement on the first touch sensor section at a second cranial landmark comprises pressing the first strip arrangement at Inion point.

According to one particular embodiment of the invention, placing the second strip arrangement over the head of the patient comprises placing the second strip arrangement along a line covering both Tragus landmarks; and wherein pressing the second strip arrangement at a lateral cranial landmark comprises pressing the second strip arrangement at Tragus point.

Optionally, one embodiment of the invention further comprises an initial step of placing one strip arrangement along a line covering both Tragus for obtaining a central head reference point by the control module, wherein the obtained central head reference point guides the subsequent placement of the same or other strip arrangement along the line covering Inion and Nasion.

Additionally, one embodiment of the invention further comprises illuminating each location determined for electrode placement of the LED strips with different colors and brightness based on the electrode placement scheme previously set; and wherein a location for electrode placement is located between two LEDs of any flexible LED strip, further comprising illuminating the nearest LED to the location with higher brightness and the furthest LED with lower brightness.

There are several tests in which present invention is useful and all involve the need for a precise placement of record or stimulation electrodes on the scalp: auditory, visual and somatosensorial evoked potentials; electroencephalography (EEG) and its variants (electroencephalography with integration, quantitative-EEG) amplitude polysomnography, and intraoperative neurophysiological monitoring among others. Present invention can be used both in adults and in pediatric or even neonatal population. Different embodiments of the invention are provided with different lengths, each intended for a specific population group (adults, pediatric or neonatal).

Moreover, present invention offers great accuracy and reliability because of the following advantages: elimination of human errors in calculations of 10-20 system; easier measurement of cranial landmarks. "Nasion-Inion" and "Tragus (LPA)-Tragus (RPA)" distances by the touch sensor; and precise location of key points to locate electrodes, such us the indicated in the 10-20 system positioning, by illuminating the LEDs in its locations following a established code of color and brightness.

Apart from placing electrodes to record bioelectric activity, there are other specific points that need to be located on the cranial surface for treatment purposes. For example, with repetitive transcranial magnetic stimulation (applied on F3) for the treatment of resistant chronic depression or for surgery purposes (Kocher's point). Those specific locations for specific treatments on the cranial surface can be matched with specific electrode positions of the electrode placement scheme. Thus, the control module will eventually illuminate the flexible LED strip at the equivalent electrode position, but not for placing any electrode but for the specific treatment of interest. Therefore, the present invention is useful for finding the location to apply rTMS or any other therapy/surgery that need to be located in a specific location from the cranial surface that can be related to International 10-20, 10-10 or 10-5 system.

Therefore, another aspect of present invention refers to the use of the system of present invention for locating a specific point for a specific treatment, where the specific point is equivalent to one location of the electrode placement scheme previously set.

BRIEF DESCRIPTION OF THE DRAWINGS

The terms Fig., Figs., Figure, and Figures are used interchangeably to refer to the corresponding figures in the drawings.

To complete the description and in order to give a better understanding of the features of the invention, this specification is accompanied by a series of drawings that are an integral part of the same, wherein the following has been represented for illustration purposes and without limitation:

FIG. 8D shows a flow diagram of the steps to locate any electrode position based on the previous measurements of cranial perimeter together with the Inion-Nasion and Tragus-Tragus.

DESCRIPTION OF THE INVENTION

Figure 1:
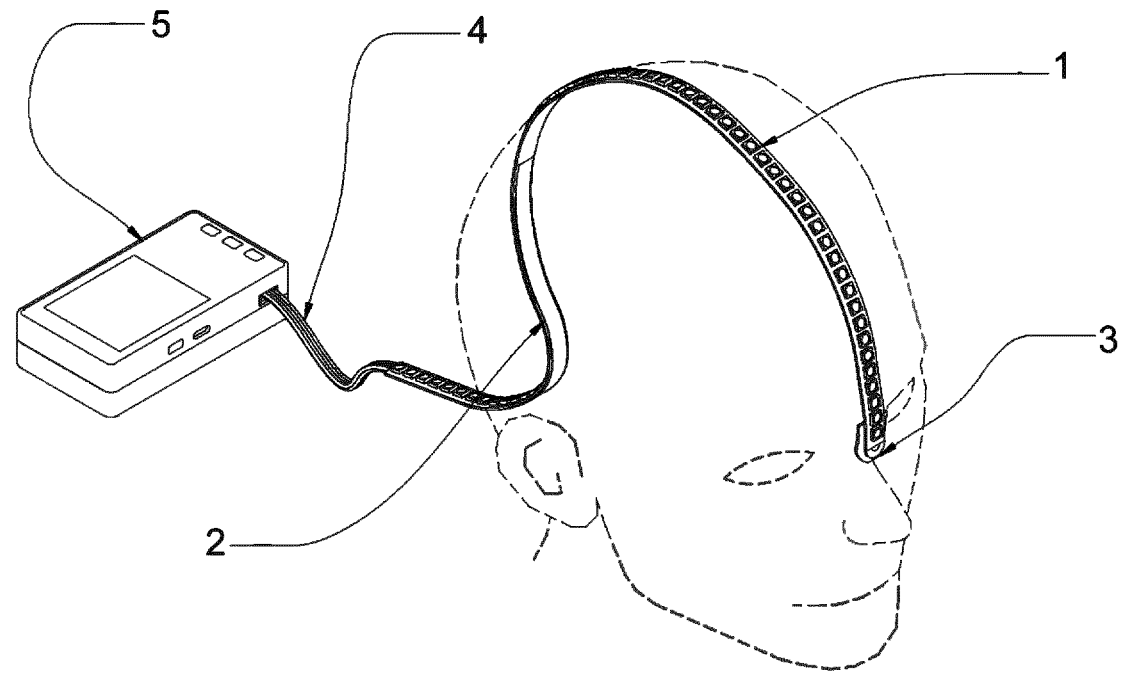
FIG. 1 shows a perspective front view of a first exemplary embodiment of the invention comprising one strip placed between Nasion and Inion.
Figure 2:
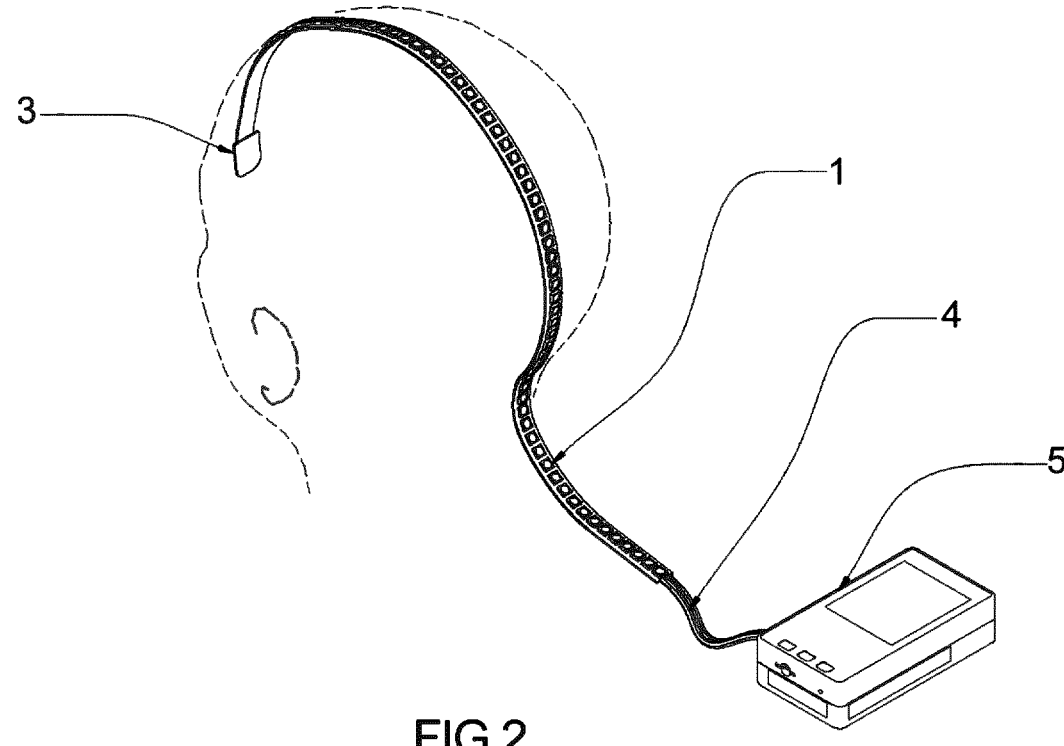
FIG. 2 shows a perspective rear view of the first exemplary embodiment of the invention comprising one strip placed between Nasion and Inion.

Present invention is based on a low-cost technology that allows an easy, quick and precise placement of electrodes for EEG.

The system of present invention is based on touch sensors for measuring the distance between basic cranial landmarks: Inion, Nasion and Tragus (LPA and RPA), and LEDs for illuminating with different brightness and color the correct position of the electrodes. The measure via touch of anatomical points is made through a ThinPot potentiometer that is a linear soft membrane potentiometer used for tracking position and acquiring the preferred output in a variety of applications. It offers a low form factor of less than 0.5 mm, making it one of the thinnest linear sensor available today.

The use of the invention is simple and only a few touches by specific staff at already well-know established points (Inion, Nasion, Tragus) in the head are needed. With the touch of the points, the electronic central unit calculates the correct position of the electrodes and will illuminate the corresponding LEDs with different color and brightness for signaling the key points (Cz, Fz, Pz, C3, C4 among others) to locate the electrodes.

The simplest embodiment of present invention comprises only one strip (made up of the LED strip and the linear sensor), so the user would need to mark the illuminated points with a marker and then moving the strip from a first position covering the line tragus-tragus to a second position covering the line inion-nasion in order to cover all the key points. The one strip embodiment is useful for patients with limited fixing possibilities, as neonates or patients with other devices covering ears or neck.

FIGS. 1-4 show the embodiment of the device with only one strip. The arrangement of a LED strip and a touch sensor may be referred as "strip". In this embodiment the elements of the device are a LED strip 1, a touch sensor 2 (linear soft membrane potentiometer), an adhesive with snap connector (pin joint) 3, wires 4 and an electronic unit 5. The electronic unit 5 comprises a screen, buttons, a microcontroller, a battery and electronics to communicate via wireless. Besides in FIG. 1 the strip is located between Inion and Nasion, but the same strip can be located between left preauricular (LPA or left Tragus) and right preauricular (RPA or right Tragus) to locate all electrode positions required.

The LED strip 1 is made of a flexible material and has a length to cover the majority of the adult cranial dimensions (for pediatric and newborns other embodiments with shorter lengths will be used).

The touch sensor 2 (which is linear soft membrane potentiometer) is attached on the interior part of the final part of LED strip. By pressing down on any part of the touch sensor, the resistance linearly changes allowing the user to very accurately calculate the relative position on the strip. The length of the touch sensor covers the difference between the majorities of the adult cranial dimensions. Since the pressure on the cranial landmark is only needed in one end of the LED strip 1, the length of the touch sensor 2 is reduced to the last 50-200 mm of the LED strip 1. Advantageously, providing the touch sensor 2 only in the last part of the LED strip 1 avoids errors of involuntary contacts that could be detected as touches by the microcontroller (for example in the most curved parts or while manipulating the end with the snap connector). The touch to identify a cranial landmark can be directly done by a small force (usually 1-3 Newtons) with a finger or a wiper on the outside part of the LED strip 1 to make a pressure between the scalp or tragus and the touch sensor. If for some reason (skin injury or others) the pressure cannot be applied to the skin, the user will only need to locate the cranial landmark and after move away the strip and press it on the located anatomical position with two fingers or with a wiper and a rigid surface.

Figures 3A, 3B:
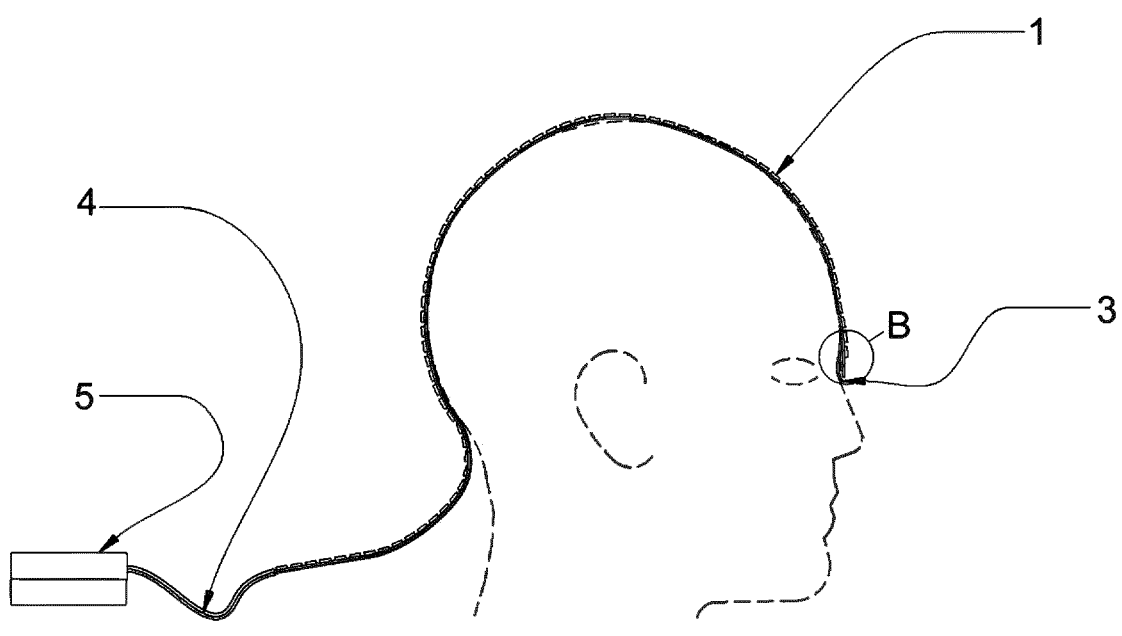
FIG. 3A shows a side view of the first exemplary embodiment of the invention comprising one strip placed between Nasion and Inion.
FIG. 3B shows a detailed view of an adhesive with snap connector and strip.
Figure 3C:
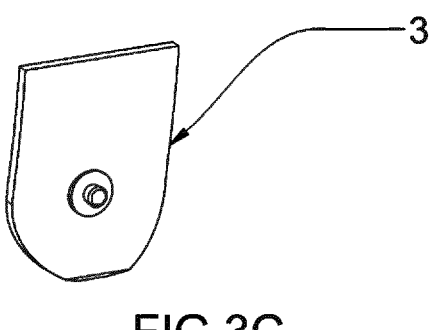
FIG. 3C shows an isometric view of the adhesive with snap connector.

FIGS. 3B and 3C show the adhesive with the snap connector 3 in detail. "B zone" is circled on FIG. 3A in order to specify the location of the snap adhesive. The snap adhesive with snap connector 3 comprises a flexible adhesive with a male snap connector, which is intended to be placed on one cranial landmark. At one end of the LED strip 1 (the end without the touch sensor) it is provided a female snap connector that fits in the male snap connector from the adhesive and so allows the LED strip 1 to be fixed in translation movements but allows rotation. The rotation is only needed if specific electrode locations have to be determined which does not happen in all neurophysiological tests. Anyway, the adhesive with the snap connector is not always needed, but it allows a single user to have a free hand to make the marks indicated by the LEDs. If two users cooperate, no adhesive is required and the strip can be held in place by light pressure with a finger.

At the end of the LED strip 1 where the touch sensor 2 is provided there is an electrical connection with a wiring 4 (needed for the supply and control of the LEDs and for the touch sensor) that connect the strip ("strip" refers to the arrangement of both the touch sensor and the LED strip) to the electronic unit 5. The length of the wiring is enough to operate the strip without the inconvenience of having the electronic unit 5 too near and avoid that the weight of the electronic unit 5 affects the handling of the strip (in FIG. 1 the wiring length is not real (shorter) just because with the dimension of the figure can be understood. The standard length of the wiring is approximately 1.5 m. The electronic unit 5 comprises a screen, where the user may choose the configuration with one or two strips and the test to perform. After that, the user will be guided for each step to follow in order to avoid human errors regarding the electrode locations. The buttons are used to navigate in the screen and choose the options displayed. The microcontroller is the one that transforms the analogic data from the touch sensor 2 to a measure and also do the calculations following the 10-20 international system (or another system uploaded to the microcontroller) to illuminate the LEDs according to the measure performed.

In one alternative embodiment of the invention, the wiring length is reduced, and a smallest electronic unit (not shown in figures) is used. The small electronic unit comprises the same elements as the standard electronics unit, but the battery and screen are smaller to reduce the dimensions that can hinder the handling in some situations. In the embodiment with the small electronic unit, the user can connect via a wireless communication to better see the screen in an external screen from another device such us a smartphone or a computer.

The LED strip 1 is addressable and each LED can be individually controlled with brightness and color. The microcontroller determines to illuminate one LED if the position calculation result is located near a LED position or two LEDs (with different brightness) if the position calculation result is between two LEDs. For example, in an embodiment where the LEDs have a square size of 5 mm and a spacing of 7 mm between LEDs (center to center), if the position calculation result differs a distance minor than 2.5 mm from a LED center, only one LED will be illuminated. If the calculation result differs a distance between 2.6 and 3.5 mm from a LED center, then two LEDs with different brightness will be illuminated to allow the user to mark the electrode position between LEDs. After the test is performed the user is asked to export the results. The results may be exported to a memory of the device (SD card) and also if a wireless connection is available, via WiFi or BLE (Bluetooth) with other devices such as computers or smartphones.

Figure 3D:
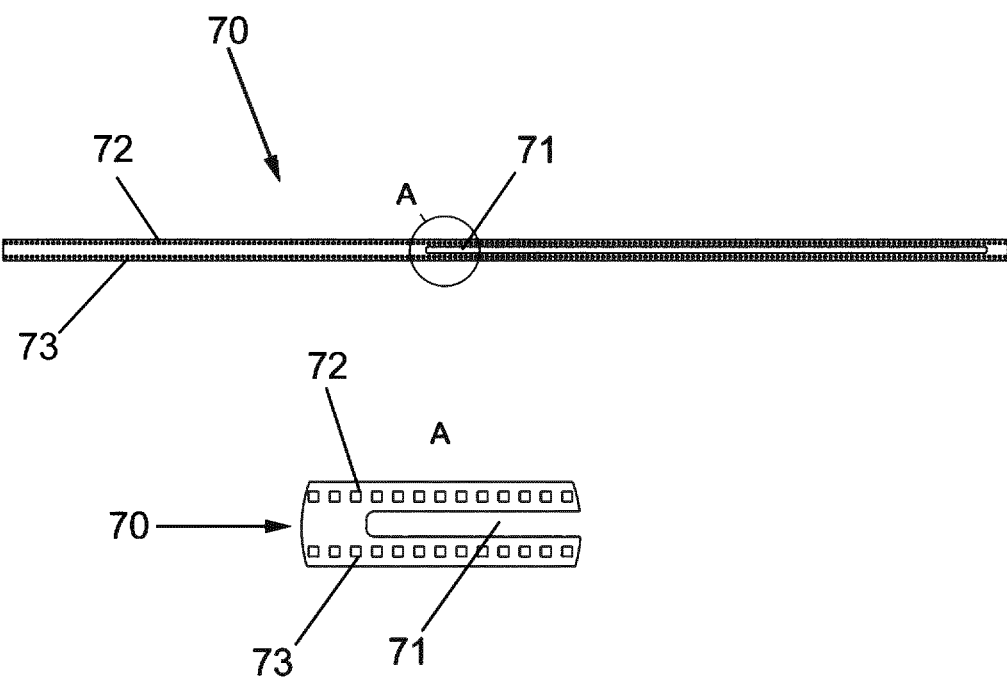
FIG. 3D shows a view of a strip embodiment with a central slot for marking purposes and two rows of leds.
Figure 4:
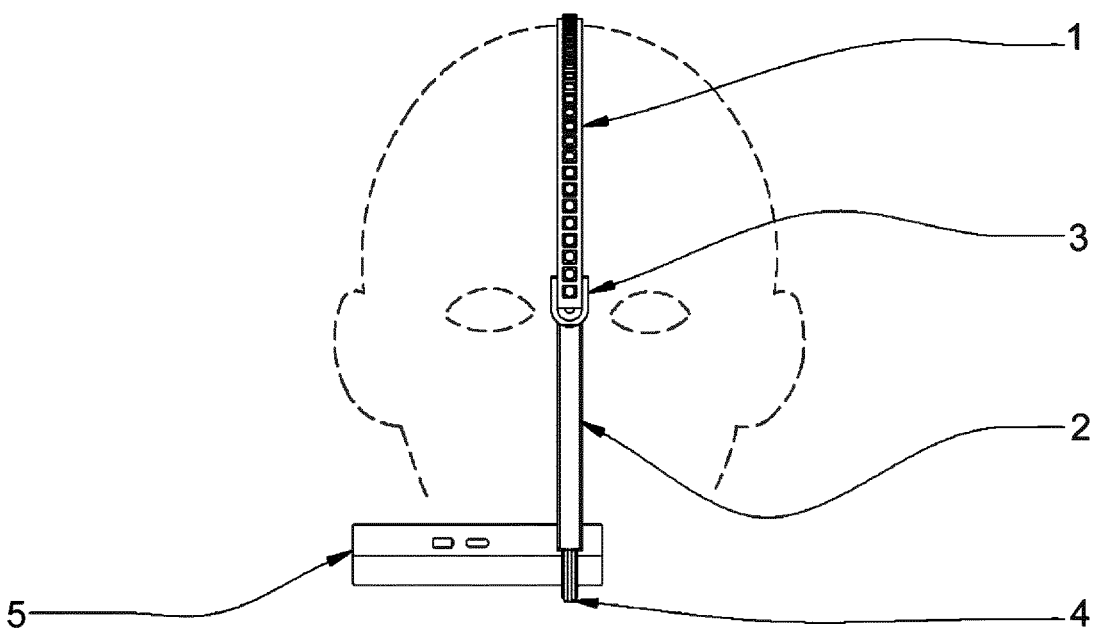
FIG. 4 shows a front view of a first exemplary embodiment of the invention comprising one strip placed between Nasion and Inion.

FIG. 3D shows view of a strip embodiment 70 with a central slot 71 for marking purposes and two rows of leds 72, 73. The central slot 71 allows the medical staff to mark the locations without moving the strip, where the two led rows 72, 73 indicate the locations in the same way (illuminating the leds) as the LED strip embodiments 1, 6 with one row of leds.

Figure 5:
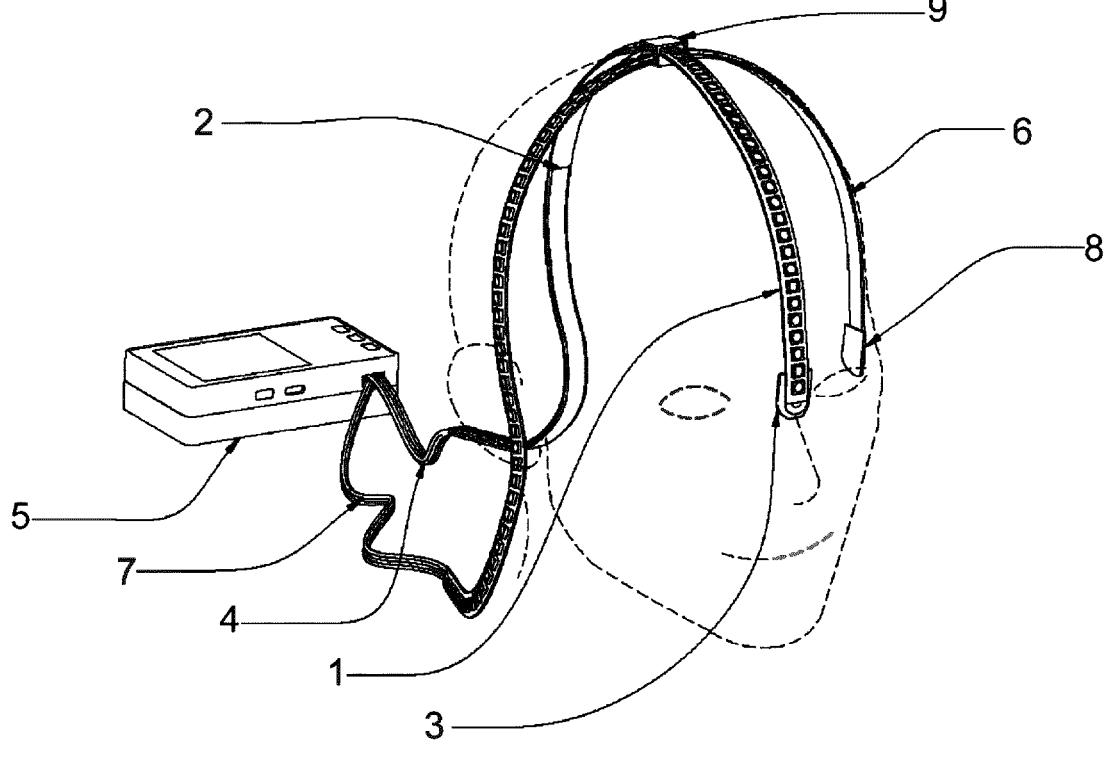
FIG. 5 shows a perspective front view of a second exemplary embodiment of the invention comprising two strips.
Figure 6:
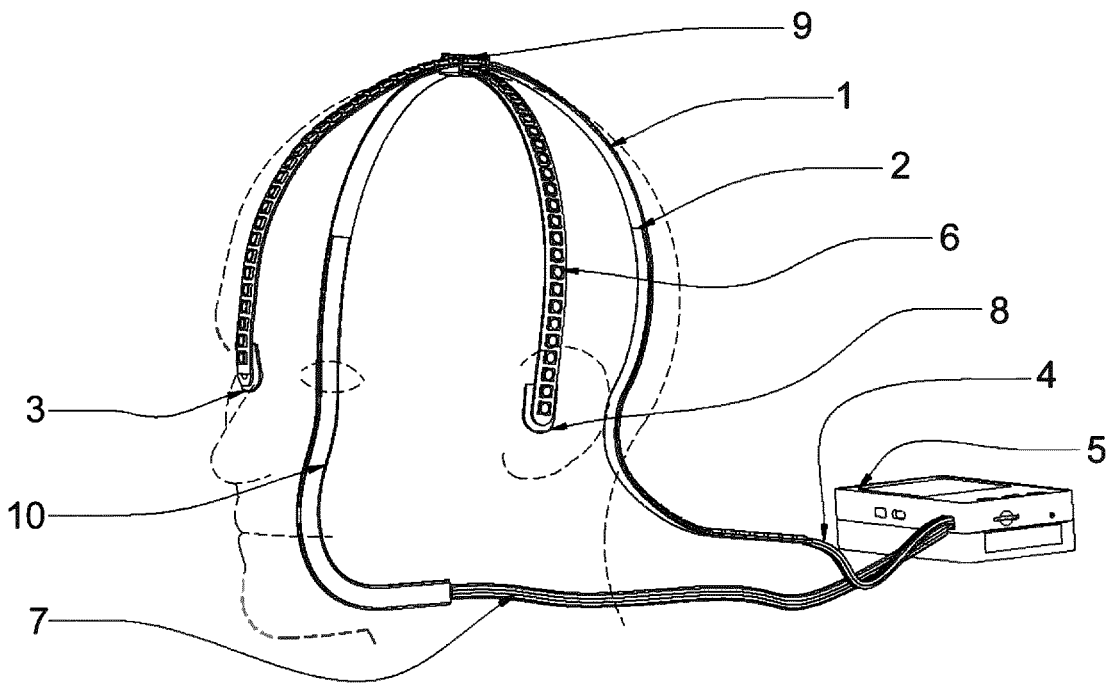
FIG. 6 shows another perspective front view of the second exemplary embodiment of the invention comprising two strips.

FIGS. 5 and 6 refer to another embodiment of the invention where a cross-shaped arrangement of two strips 1, 6 is shown. Each of the strips consists of a same sandwich strip arrangement disclosed for the one strip embodiment of FIGS. 1-4, so each strip comprises a touch sensor 2, 10 means arranged along the final part of a flexible LED strip and a flexible LED strip 1, 6.

To fix the position of the beginning of the strips with the cranial landmark, an adhesive with snap connector 3, 8 (same one as the already described for the one strip embodiment of FIGS. 1-4) is provided in this embodiment to be adhered to the patient, but other fixing methods can be used. If adhesives are used the user holds the end of the strip with one hand while marks the positions of the electrodes with the other hand. If the patient is lying on his back, strip 1 only needs to be held in Nasion.

Alternatively to the adhesive means, in order to fix the strip 1 in the Nasion, other holding means can be used. For example, in one embodiment the strip is attached to glasses to hold one end of the strip with the Nasion.

Regarding the strip 6, alternatively to the adhesive means 8, in order to fix the position of strip 6 to both sides of head patient, the strip 6 may comprise a set of elastic bands adaptable to the ear of the patient. Besides of the elastic bands, other standard elastic or adjustable systems (such as any standard EEG cap holding system) can be used to fix the position of strip 6.

The two strips 1, 6 are connected to a microprocessor (not shown) inside the electronic unit 5. The microprocessor is configured for detecting the location where the user is pressing the touch sensor 2, 10, which is a linear soft membrane potentiometer. Therefore, the user should place strip 6 adjusted to the ears of the user on the head of the patient covering tragus reference points. Once the strip 6 is in contact with the head, the user should align the beginning of the strip with one tragus and press the strip at the other tragus point by applying a pressure directly in the strip or if the patient is sensitive by pressing the strip with two fingers. (This initial procedure is recommended to indicate the central head line as reference for placing strip 1 and avoiding eventual errors due to the central position of Inion cranial landmark, but this initial procedure can be skipped in some embodiments and directly start by placing strip 1 over the line Nasion-Inion without any other reference). After that, the user should place strip 1 covering the Inion and Nasion reference points and aligning them with the central position established in the previous step. The beginning of the strip 1 has to be placed on the Nasion and press the strip at Inion point by applying a pressure directly in the strip or if the patient is sensitive by pressing the strip with two fingers. Then, the microprocessor measures the distance between nasion (the beginning of the strip) and inion (pressure point). According to an electrode placement scheme previously set on the microprocessor (usually the international 10-20 system), it calculates the distance of the key points form inion or nasion. Finally, the microprocessor commands the LED strip to illuminate the location of each key point.

Once strip 1 is placed on the head and key points between inion and nasion are illuminated, the user should align central point of strip 6 with central point of strip 1. Then, strip 2 will illuminate the key points in a perpendicular direction to be marked.

The strip 6 in the same way as strip 1 has a wiring 7 and a touch sensor 10. To join the two strips 1, 6, but letting relative movement between them to align the central position (Cz) of both strips, a joint 9 is used. The use of the joint 9 involves a small distance between the scalp and the central point in the Nasion-Inion strip. If the user chooses the configuration with two strips, the calculations done in the microcontroller already take into account this gap and errors due to this gap are minimized in the electrode placement procedure.

The LED strips 1, 6 can produce different brightness and different colors. In one embodiment of present invention, the microprocessor associates certain key points with certain colors and level of brightness for an easier guidance of the user to locate the electrodes. Specifically, the brightness helps to adapt to different working light conditions and also it increases accuracy because in case the point to be marked is located between two LEDs and not equidistant from both LEDs, the nearest LED has higher brightness than the other LED. Preferably, the distance between LEDs may be any value between 7 mm and 2 mm, having the capacity to indicate different positions with an accuracy higher than half-distance between LEDs (from 3.5 mm for the case of 7 mm between LEDs to 1 mm for the case of 2 mm between LEDs).

FIGS. 7 and 8A-8D show the guided process through the information displayed in the device screen of one particular embodiment of the invention. This process may be remotely managed by a remote user via any smart device such as a computer or a smartphone, with access to the electronic unit through a wireless connection.

Figure 7:
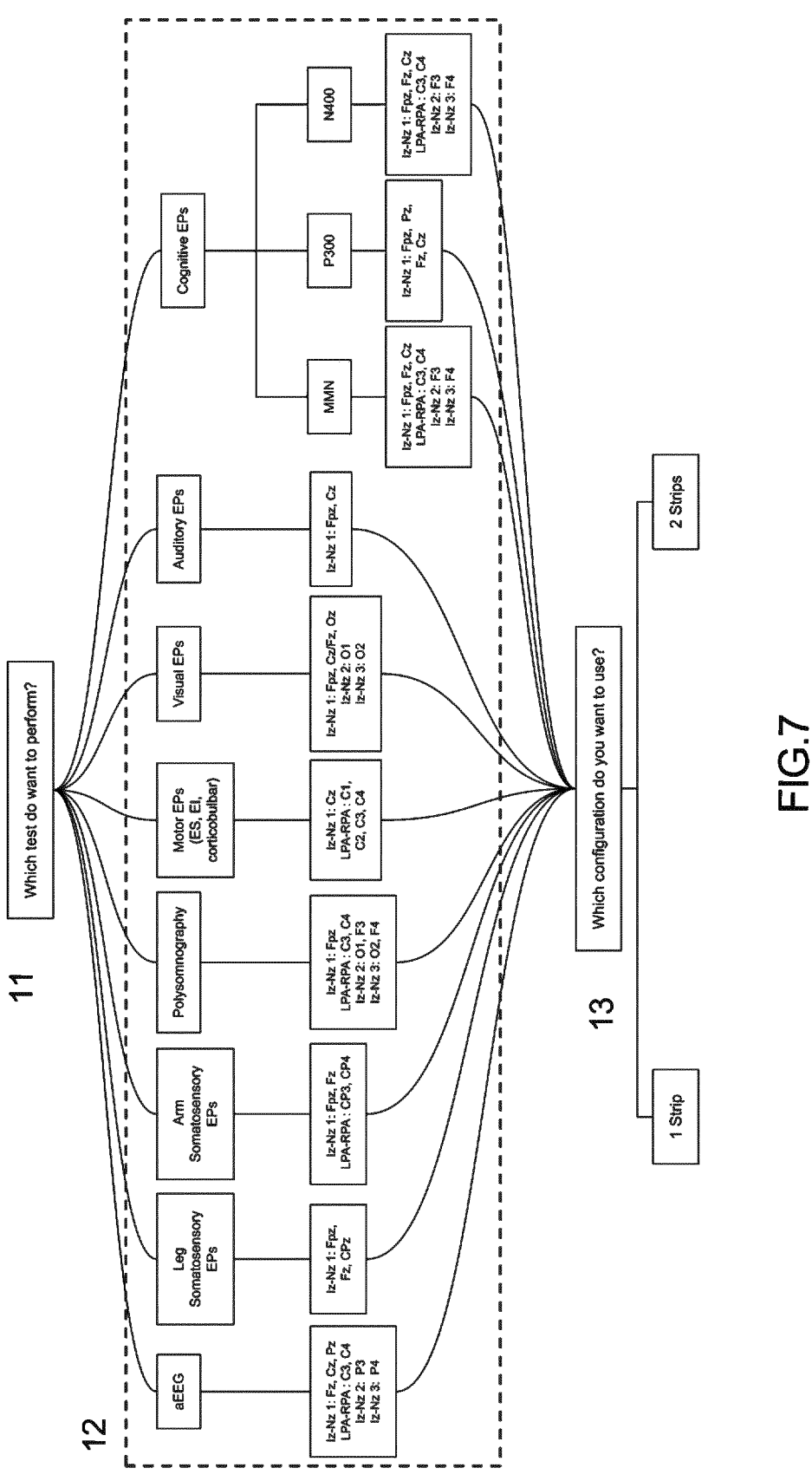
FIG. 7 shows an example of the tests offered for user selection, such as aEEG, somatosensory EPs, polysomnography, motor EPs, visual EPs, auditory EPs or cognitive EPs, and its corresponding electrodes to locate.

Specifically, FIG. 7 shows an example of the tests, such as aEEG, somatosensory EPs, polysomnography, motor EPs, visual EPs, auditory EPs or cognitive EPs, and its corresponding electrodes to locate, but any other electrodes positions can be located. Once the device is started the user is asked (step 11) about the test to perform. After test selection (step 12) the user can choose (step 13) between using the version with one or two strips (different embodiments). Then, all instructions showed in the screen follow the flow diagrams from FIGS. 8A and 8B (one and two strips configuration respectively).

Figure 8A:
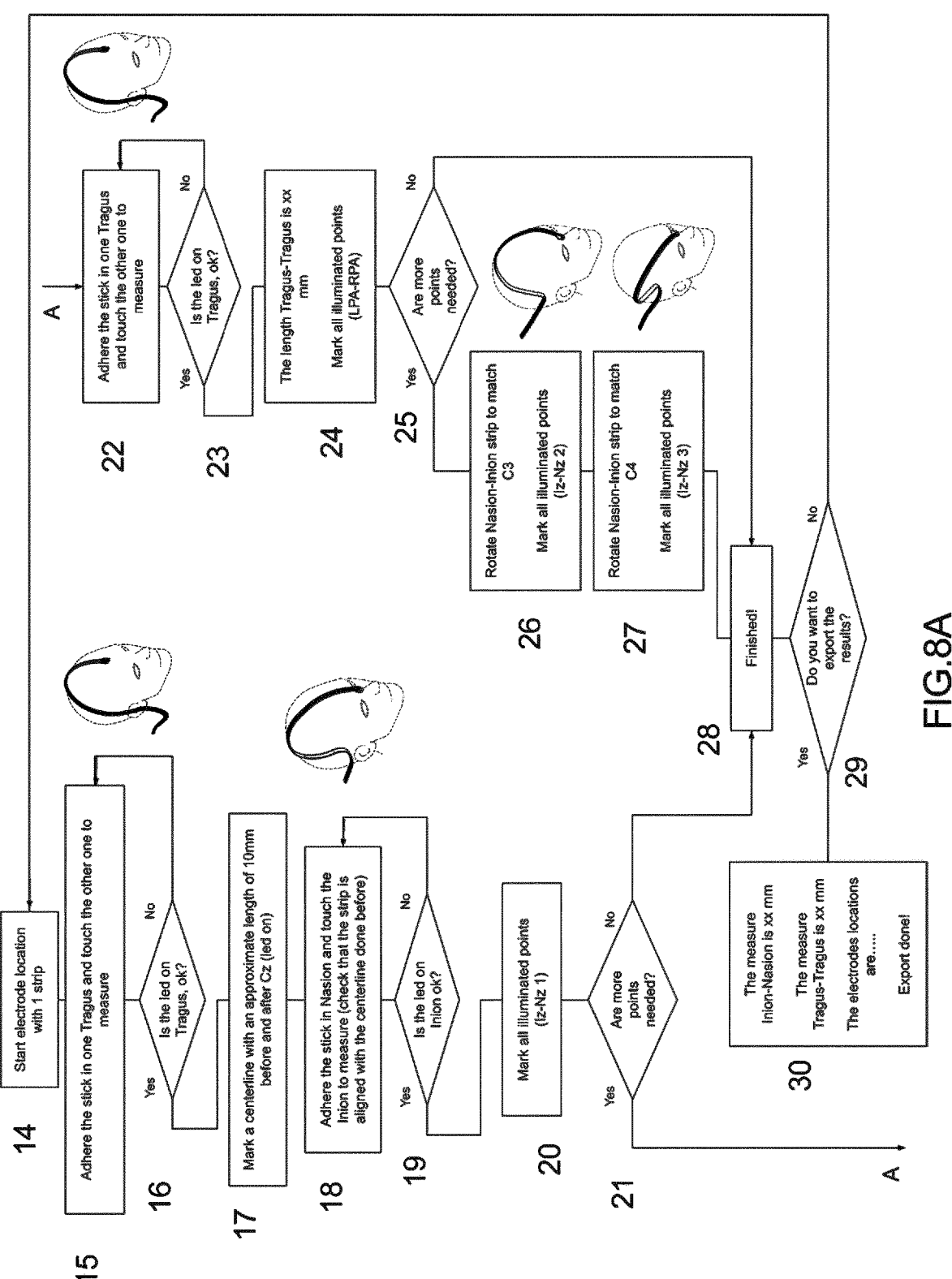
FIG. 8A shows a flow diagram of the guided process through the information displayed in the device screen for the embodiment of one strip.
Figure 8B:
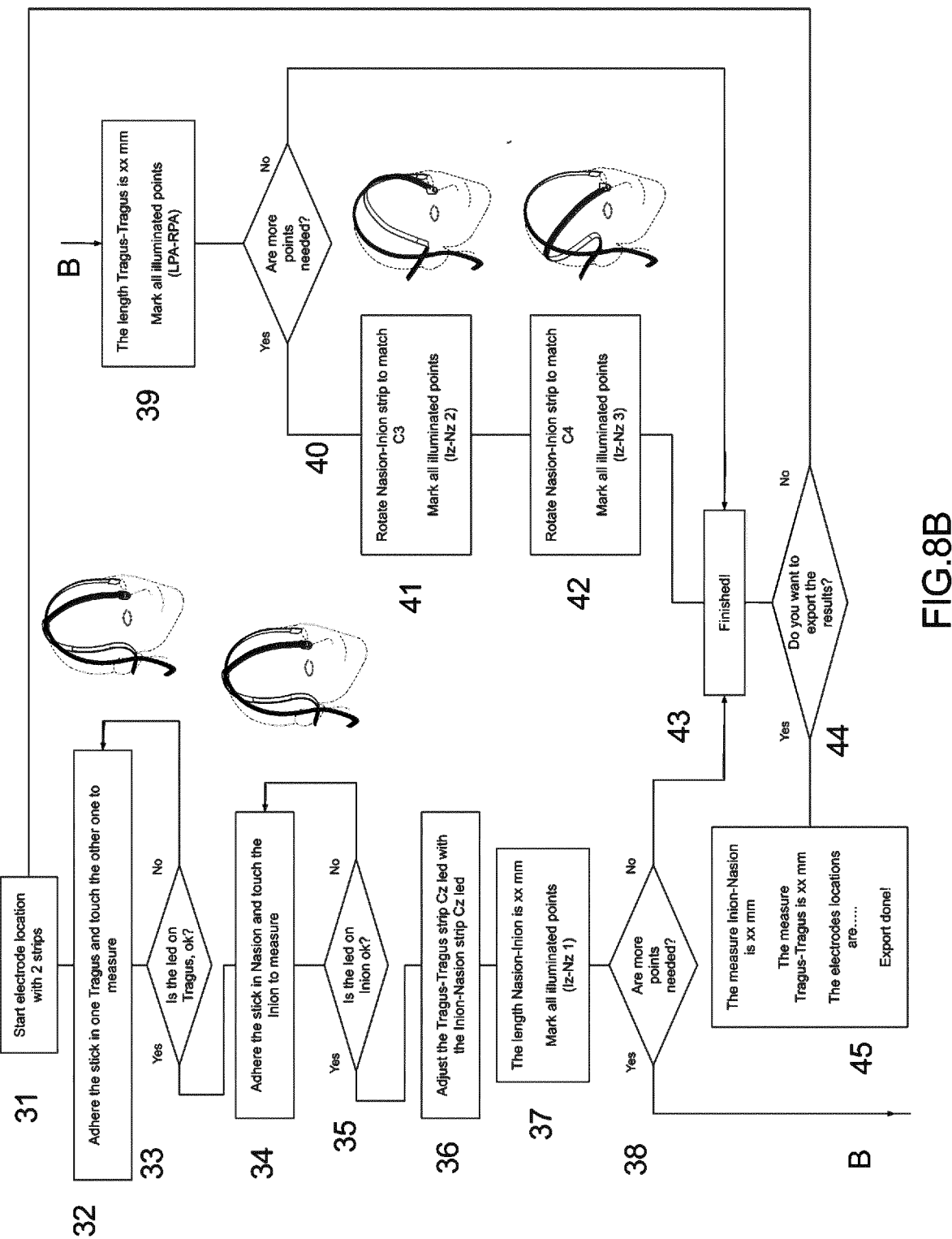
FIG. 8B shows a flow diagram of the guided process through the information displayed in the device screen for the embodiment of two strips.
Figure 8C:
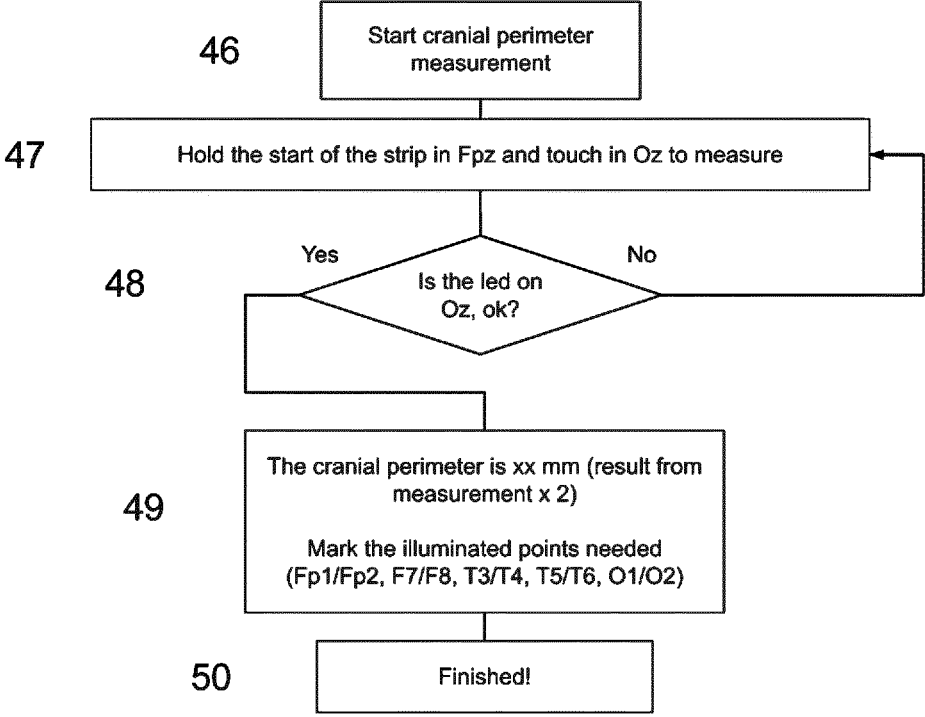
FIG. 8C shows a flow diagram of the steps to measure the cranial perimeter.

After finishing standard process (FIGS. 8A and 8B), the user has the option to measure the cranial perimeter to locate some points not identified with the standard tests (FIG. 8C). Additionally, the user can locate any electrode position from international system 10:20, 10:10, 10:5 or a custom system using the LED strips to mark the position (FIG. 8D). The location of any electrode position is based on mathematical calculations performed by the microprocessor using the equations proposed by Beam et. al. or any other calculation based on the measurements Tragus-Tragus, Nasion-Inion and cranial perimeter.

Figure 9A:
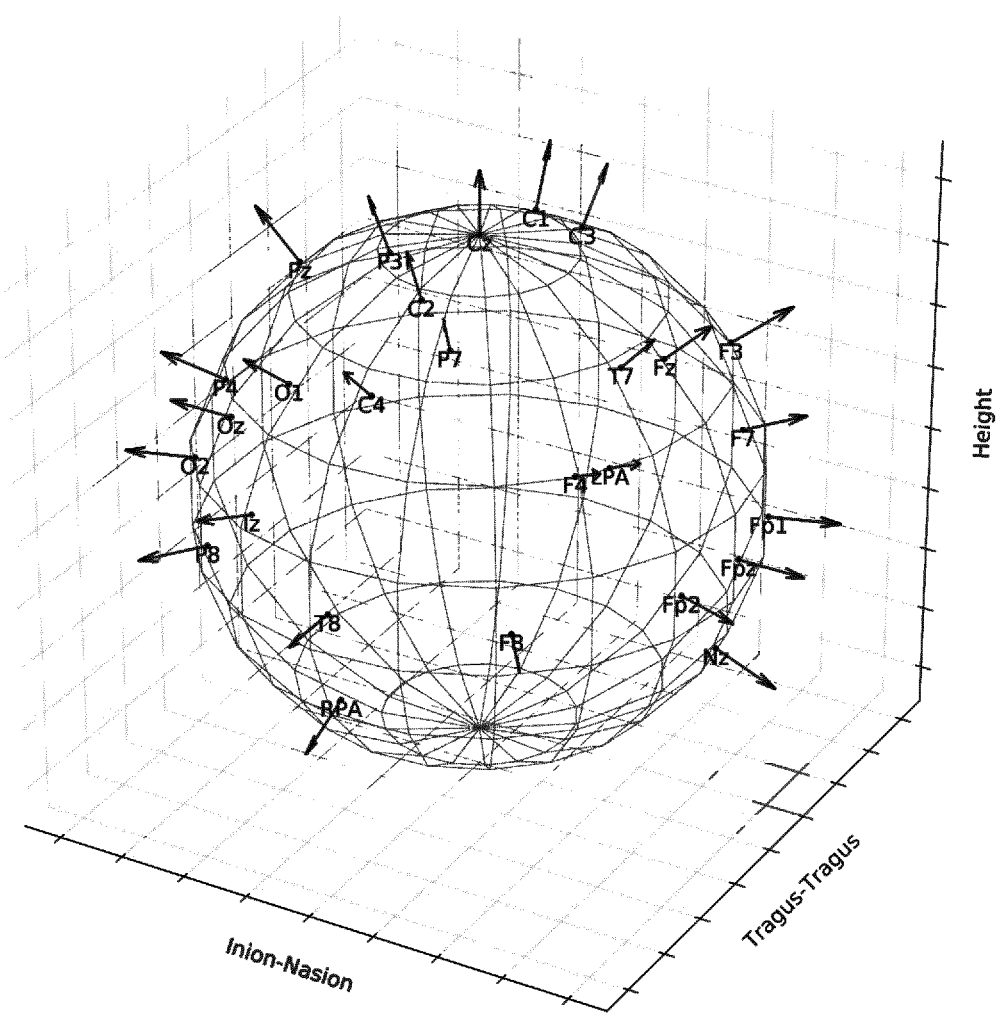
FIG. 9A shows main electrodes locations for general tests, specifically system 10-20, in sphere model
Figure 9B:
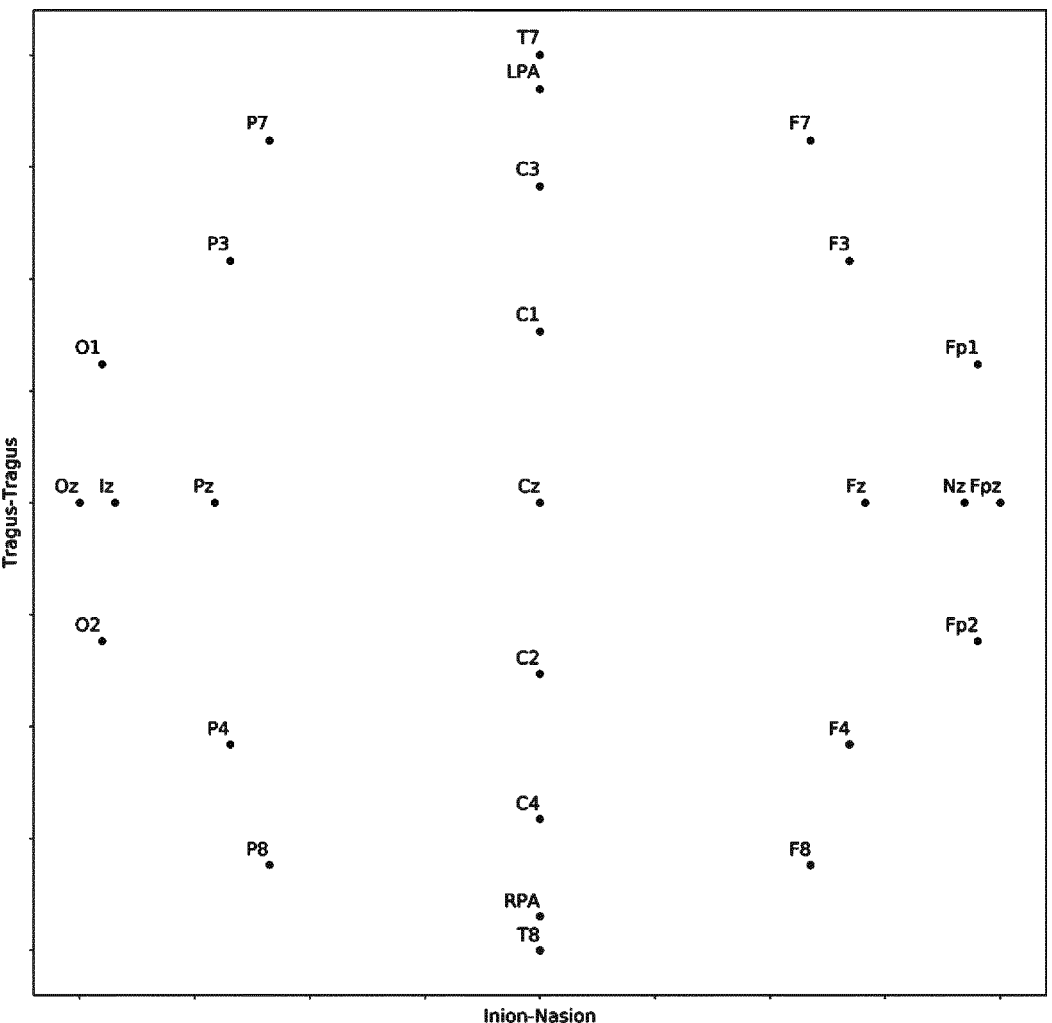
FIG. 9B shows main electrodes locations for general tests, specifically system 10-20, from a top view.

FIG. 8A shows the steps needed to perform a location with the embodiment of one strip configuration. Once the procedure starts (step 14), to reduce the error from misaligning the Inion with the centreline, the first operation is to mark a centreline with the Tragus-Tragus strip (steps 15, 16, 17). Once this centreline is done the firsts electrodes can be located with the Nasion-Inion. These steps could be avoided and directly start on step 18. After the user touches on the Inion position, the microcontroller recognizes the touch and illuminates the LED or LEDs corresponding to Inion position (step 19). If the user agrees on the Inion location the microcontroller illuminate the positions to mark in the Nasion-Inion direction (step 20). In some tests, such as the leg somatosensory evoked potentials or the auditory evoked potentials, the electrodes to locate finishes (step 28) because there are only locations on the Nasion-Inion direction, but on the majority of the tests, the user needs to locate electrodes on the Tragus-Tragus direction (step 21). Because of that, steps 22 to 24 are needed. Once the strip is placed in one Tragus, aligned with Cz (previously marked) and the user touches on the other Tragus, the microcontroller recognizes the touch and illuminates the LED or LEDs corresponding to the Tragus touched (step 22). If the user agrees on the Tragus location the microcontroller illuminate the positions to mark in the Tragus-Tragus direction (step 23 and 24). Depending on the test chosen, the process can finalize (step 28) or continue (step 25). If more positions are needed to locate, then the strip has to be placed between the Nasion and the Inion but instead to be aligned to the centreline, has to rotate/pivote to be aligned with C3/C4 to locate the remaining electrode locations (Fp1/Fp2, F3/F4, P3/P4 and O1/O2) (steps 26 and 27). In the same way, apart from placing the strip between Tragus and Tragus aligned with Cz. The strip can be pivoted/rotated to align the central position with Fz or Pz to locate the positions of the electrodes corresponding to F3/F4 or P3/P4 (not used in FIG. 9 because is better to pivot the Inion-Nasion strip, but possible for locating specific locations of electrodes).

Once all positions are marked the user has the option to save/export the results to the SD card and send it to an external wireless device (Bluetooth or Wifi) (steps 29 and 30).

FIG. 8B shows the steps needed to perform a location with the embodiment of two strip configuration. Once the procedure starts (step 31), to reduce the error from misaligning the Inion with the centreline, the first operation is to illuminate the centreline with the Tragus-Tragus strip (steps 32 and 33). When the strip is placed in one Tragus and the user touches on the other Tragus, the microcontroller recognizes the touch and illuminates the LED or LEDs corresponding to the Tragus touched (step 33). If the user agrees on the Tragus location the microcontroller illuminate the centreline and other positions on the strip but the user cannot mark the position because Cz is not known. Then the Nasion-Inion strip is placed (aligned with the Nasion and the centreline) by adhering the stick of the holding means in Nasion and touching on the Inion position (step 34), the microcontroller recognizes the touch and illuminates the LED or LEDs corresponding to Inion position (step 35). If the user agrees on the Inion location a message remaining the necessity to align the central position of both strips is shown (step 36) and the microcontroller illuminate the positions to mark in the Nasion-Inion and Tragus-Tragus direction (steps 37 and 39). Depending on the test chosen, the process can finalize (step 43) or continue (steps 38 and 40). If more positions are needed to locate, then the strip has to be placed between the Nasion and the Inion but instead to be aligned to the centreline, is rotated/pivoted to be aligned with C3/C4 to locate the remaining electrode locations (Fp1/Fp2, F3/F4, P3/P4 and O1/O2) (steps 41 and 42). In the same way, apart from placing the strip between Tragus and Tragus aligned with Cz. The strip can be pivoted/rotated to align the central position with Fz or Pz to locate the positions of the electrodes corresponding to F3/F4 or P3/P4 (not used in FIG. 9 because is better to pivot the Inion-Nasion strip but possible for locating specific locations of electrodes).

Once all positions are marked the user has the option to save/export the results to the SD card and send it to an external wireless device (Bluetooth or Wifi) (steps 44 and 45).

Additionally, in any configuration of one or two strips of present invention, once FpZ and Oz have been determined, any strip 1, 6 can be used to measure half of the cranial perimeter. FIG. 8C shows the steps to measure the cranial perimeter and the locations that can be marked according to system 10-20 through the cranial perimeter.

Thus, once the procedure to measure the cranial perimeter starts (step 46), the screen show a message to the user for holding one end of the strip in Fpz (it can be done only holding with the hand or adhering the adhesive with the snap connector) and touching in Oz (step 47). The user needs to confirm that the LED is on Oz, otherwise the method go back to step 47 again. Once the LED is on Oz (step 48), the microcontroller doubles the distance measured to obtain the cranial perimeter and command the LED strip to illuminate the points needed (Fp1/Fp2, F7/F8, T3/T4, T5T6, O1/O2) at step 49. Then the measurement of cranial perimeter is finished (step 50).

Figure 10A:
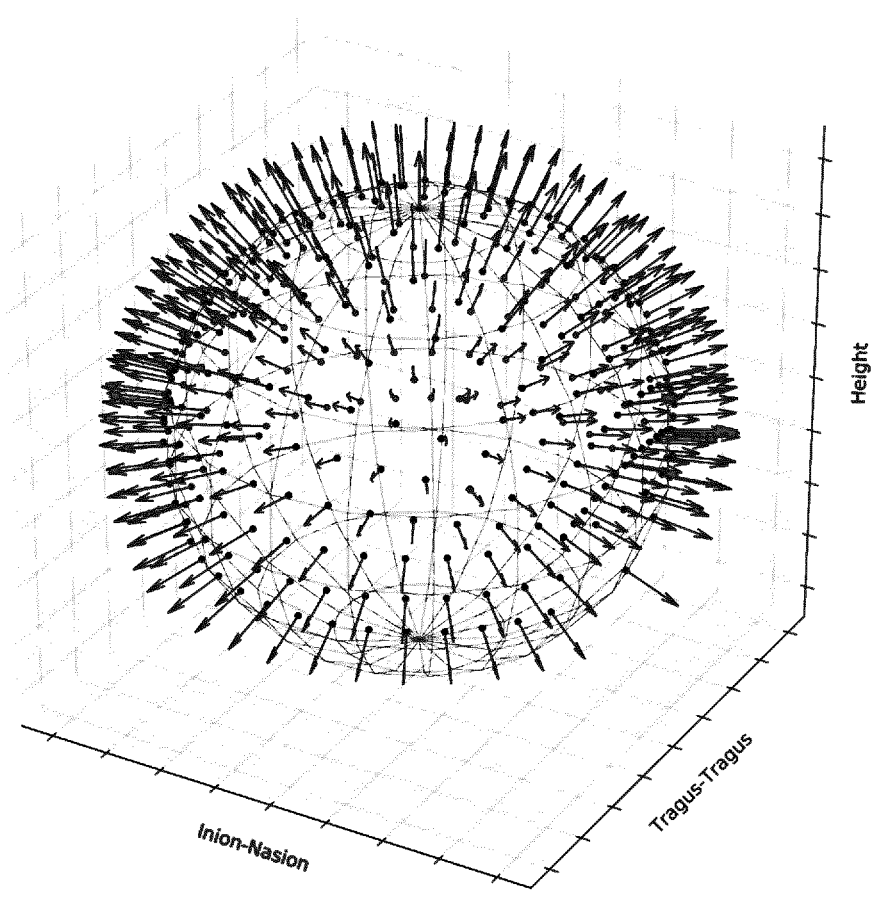
FIG. 10A shows main electrodes locations for general tests, specifically system 10-5, in sphere model
Figure 10B:
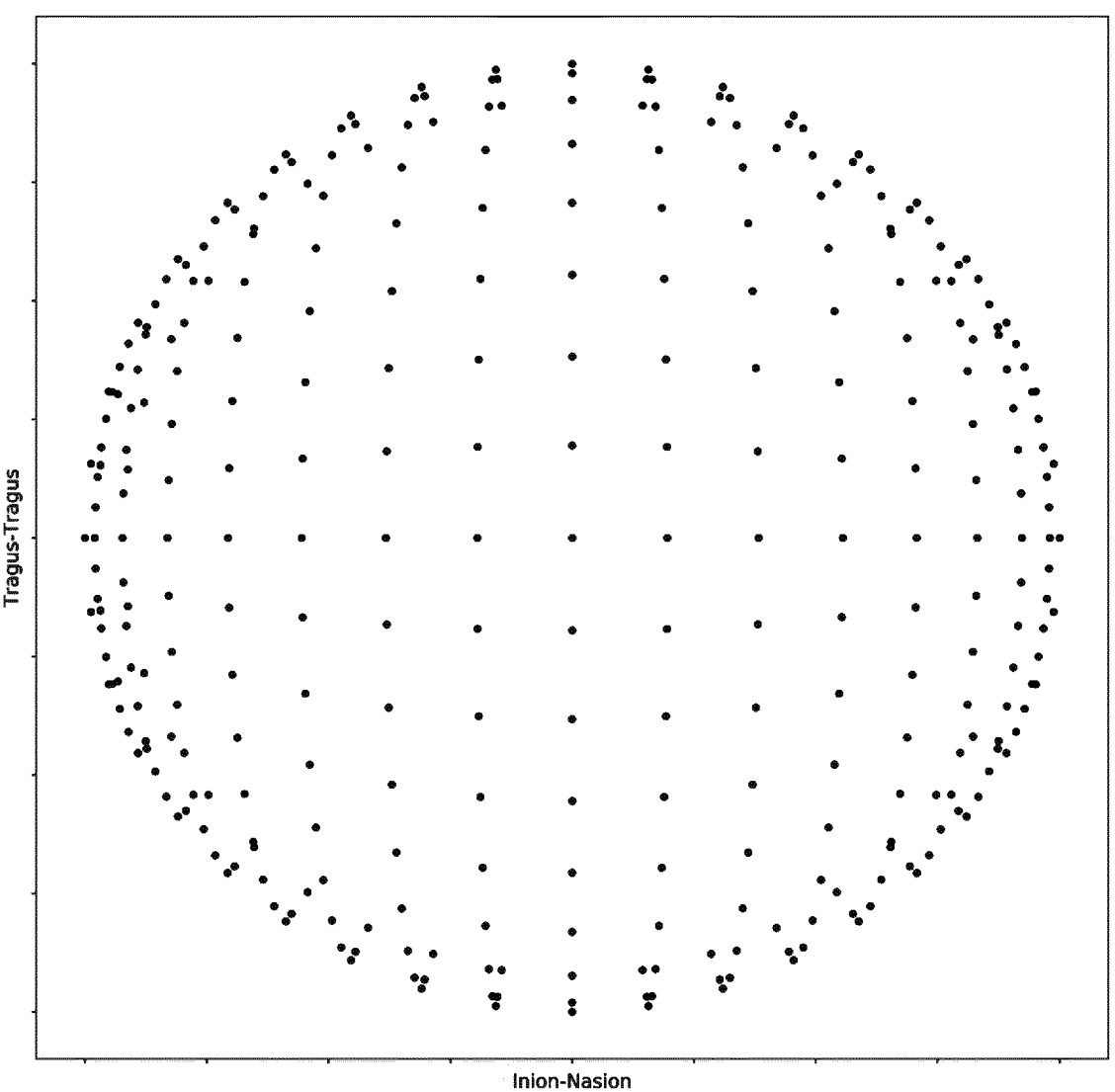
FIG. 10B shows main electrodes locations for general tests, specifically system 10-5, from a top view.

The use of the cranial perimeter together with the Inion-Nasion and Tragus-Tragus lengths allows via mathematical calculations performed by the microprocessor to locate any point in the scalp. Because of that, if the user wants to locate any point from a custom system or from system 10-20 (shown in FIGS. 9A and 9B, where axis represents Inion-Nasion line, Tragus-Tragus line and Height), 10-10 or 10-5 (shown in FIGS. 10A and 10B, where axis represents Inion-Nasion line, Tragus-Tragus line and Height) systems that are not predefined in the selected neurophysiological test, the location can also be performed. The location of any point is based on the equations proposed by Beam et. al. in the publication "An efficient and accurate new method for locating the F3 position for prefrontal TMS applications" or any other calculation based on the measurements Tragus-Tragus, Nasion-Inion and cranial perimeter. After selecting the electrode to locate, a strip has to be placed (can be done only holding with the hand or adhering the adhesive with the snap connector) along the head circumference (cranial perimeter) with the beginning of the strip in Fpz. Then, one position will be indicated to be marked and after that, the start of the strip has to be placed in the Vertex (Cz) and the previous marked point. The position of the electrode to place will be indicated in the strip.

FIG. 8D shows the steps to locate any electrode position based on the previous measurements of cranial perimeter together with the Inion-Nasion and Tragus-Tragus. Thus, the user starts the procedure of punctual electrode location (step 51). The already obtained measures of cranial perimeter together with the Inion-Nasion and Tragus-Tragus are checked (step 52) to confirm that they all are correct (step 53), if not, the measurements need to be repeated (step 54) or the user can directly introduce the values (that could be previously taken or measured by other devices such us a measuring tape). The user is asked about the system to use (step 55), which can be selected from 10-20, 10-10, 10-5 or custom one (step 56). After that, the user is asked for the electrode location of interest (step 57). The list of possible electrode locations is displayed (step 58) as a function of the system selected. For example AF9, AF7, AF5, AF3, AF1, AFz, AF2, AF4, AF6, AF8, AF10 . . . up to 342 locations from 10-5 system or custom locations defined by the user beforehand. Then, the user is required to hold one end of the strip in Fpz and the other end at Oz and then, the microcontroller command the LED strip to illuminate the location to be marked by the user (step 59). After that, the user is required to hold one end of the strip in Cz (can be done only holding with the hand or adhering the adhesive with the snap connector) and to align the strip with the previous marked location in order to mark the illuminated point to locate the electrode (step 60) and finish the procedure (step 61).

Figure 8E:
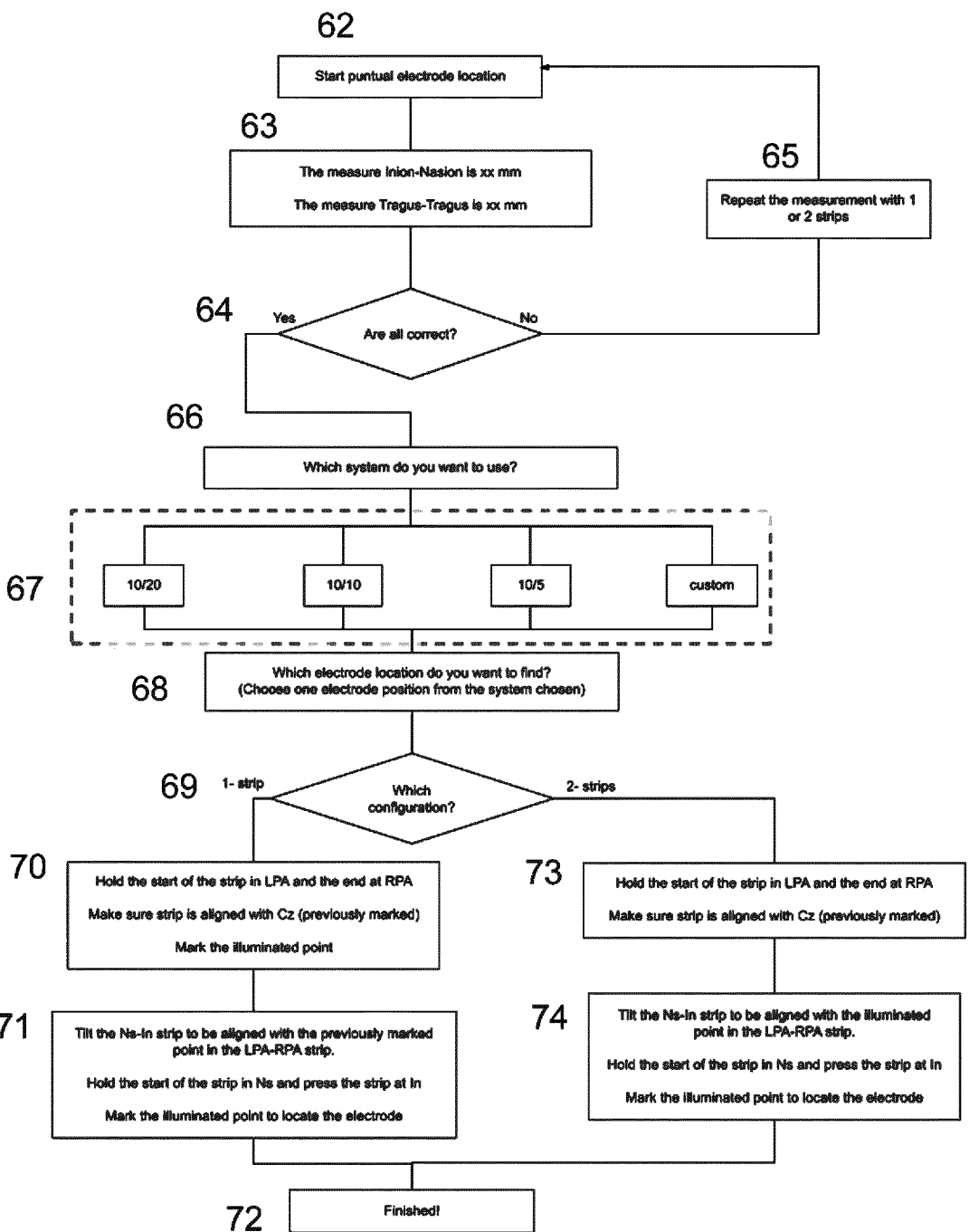
FIG. 8E shows a flow diagram of the steps to locate any electrode position based on the previous measurements of Inion-Nasion and Tragus-Tragus.

FIG. 8E shows the steps to locate any electrode position based on the previous measurements of Inion-Nasion and Tragus-Tragus. Thus, the user starts the procedure of punctual electrode location (step 62). The already obtained measures of Inion-Nasion and Tragus-Tragus are checked (step 63) to confirm that they all are correct (step 64), if not, the measurements need to be repeated (step 65) or the user can directly introduce the values (that could be previously taken or measured by other devices such us a measuring tape). The user is asked about the system to use (step 66), which can be selected from 10-20, 10-10, 10-5 or custom one (step 67). After that, the user is asked for the electrode location of interest (step 68). The list of possible electrode locations is displayed as a function of the system selected. For example, AF9, AF7, AF5, AF3, AF1, AFz, AF2, AF4, AF6, AF8, AF10 . . . up to 342 locations from 10-5 system or custom locations defined by the user beforehand. Then, the user is required for which configuration want to use (step 69), 1 or 2 strips embodiments. After that, the device explains the steps required to perform the location of the electrode position. If 1-strip embodiment is chosen the user is asked to hold one end of the strip at LPA and the other end at RPA through Cz point and then, the microcontroller command the LED strip to illuminate the location to be marked by the user (step 70). After that, the user is required to change the strip to Nasion-Inion position (can be done only holding with the hand or adhering the adhesive with the snap connector) tilted to be aligned with previous marked location in order to mark the illuminated point to locate the electrode (step 71) and finish the procedure (step 72). If 2-strip embodiment is chosen the user is asked to hold one end of the first strip (LPA-RPA) at LPA and the other end at RPA through Cz point (step 73) and then, the microcontroller command the LED strip to illuminate the location to be aligned afterwards with the second strip (Nasion-Inion). After that, the user is required to place the Nasion-Inion strip (can be done only holding with the hand or adhering the adhesive with the snap connector) tilted to be aligned with illuminated point from the first strip in order to mark the illuminated point to locate the electrode (step 74) and finish the procedure (step 72).

One embodiment of the invention takes advantage of the illuminated locations for guiding electrode placement for alternative purposes, since there are specific points of the cranial surface which are equivalent to specific electrode locations. For example, repetitive transcranial magnetic stimulation for the treatment of resistant chronic depression is applied on F3 point, or for surgery purposes (Kocher's point). Therefore, the present invention is also useful for finding the location to apply rTMS or any other therapy/surgery that need to be located in a specific location from the cranial surface that can be matched with International 10-20, 10-10 or 10-5 system.

The invention claimed is:

1. A system for guiding electrode placement on a scalp characterized by the system comprising:

a first strip arrangement comprising:

a first flexible LED strip;

a first touch sensor means arranged along a section of the first flexible LED strip configured for measuring a distance between cranial landmarks; and a control module connected to the first strip arrangement;

wherein, the control module is configured for setting a first cranial landmark at one end of the first flexible LED strip, setting a second cranial landmark where a physical touch is detected by the touch sensor means and illuminating the first flexible LED strip at least at one location for guiding electrode placement, based on the distance between the two cranial landmarks and an electrode placement scheme previously set.

2. The system according to claim 1 further comprising:

a second strip arrangement connected to the control module, the second strip arrangement comprising:

a second flexible LED strip;

a second touch sensor means arranged along a section of the second flexible LED strip; and a joint element configured for joining the first and the second strip arrangements in a cross shape, wherein the joint element allows relative perpendicular movement between them to align a central position of both strip arrangements;

wherein the control module is further configured for setting a first additional cranial landmark at one end of the second strip arrangement, setting a second additional cranial landmark where a physical touch is detected by the second touch sensor means and illuminating the second flexible LED strip at least at one location for guiding electrode placement, based on the distance between the two additional cranial landmarks and the electrode placement scheme previously set.

3. The system according to claim 2 where the second strip arrangement comprises additional holding means configured for pivot holding the second strip arrangement to a patient.

4. The system according to claim 2 further comprising a glasses-shape holder at one end of the first strip arrangement, the glasses-shape holder is configured for holding the first strip arrangement to a patient's nose at Nasion cranial landmark.

5. The system according to claim 1 wherein the control module is further configured for illuminating the first flexible LED strip at one location signaling a central head reference point.

6. The system according to claim 1 wherein the control module is further configured for matching one location of the electrode placement scheme previously set with a specific point for a specific treatment; and illuminating the flexible LED strip at the one location matched with the specific point for said specific treatment.

7. The system according to claim 1, wherein the first touch sensor means are a soft membrane potentiometer configured for measuring distance between cranial landmarks selected from Inion, Nasion and Tragus.

8. The system according to claim 1 wherein the first touch sensor means are arranged on a last section of the flexible LED strip and wherein the length of the touch sensor means is selected within a range of 5-20 cm.

9. The system according to claim 1 wherein the first strip arrangement further comprises a holding means arranged at one end of the strip arrangement, the holding means are configured for pivot holding the strip arrangement to a patient.

10. The system according to claim 8 where the holding means comprise an adhesive with a snap connector comprising a set of male and female matching connectors, wherein the female connector is adhered to the end of the strip arrangement and the male connector can be adhered to the patient at one cranial landmark.

11. The system according to claim 1 wherein the flexible LED strip comprises two parallel rows of LEDs and a central slot arranged between the two parallel rows of LEDs along a second section different from the section of the touch sensor means.

12. A method for locating a specific point on the scalp by means of the system according to claim 1, where the specific point is equivalent to one location of the electrode placement scheme previously set, wherein the method comprises pressing the touch sensor and confirming the locations through LED lighting, so that it allows guiding the precise location of each electrode by illuminating the corresponding points of the LED strip following an established color code.

13. A method for guiding electrode placement on a scalp characterized by the method comprising the following steps:

placing a first strip arrangement over the head of a patient, wherein the first strip arrangement comprises a first touch sensor means arranged along a section of a first flexible LED strip;

adjusting one end of the first strip arrangement at a first cranial landmark;

pressing the first strip arrangement on the section at a second cranial landmark;

measuring, by the first touch sensor means, the distance between the two cranial landmarks;

determining, by a control module connected to the first strip arrangement, at least one location along the first strip arrangement for electrode placement, based on the measured distance and an electrode placement scheme previously set; and illuminating the first flexible LED strip at the location for guiding electrode placement.

14. The method according to claim 13 further comprising:

placing a second strip arrangement over the head of the patient, wherein the second strip arrangement comprises a second touch sensor means arranged along a second flexible LED strip and pivot holding means;

holding an end of the second strip arrangement at a lateral cranial landmark of the patient;

pivoting the second strip arrangement until aligning with illuminated locations of the first flexible LED strip;

pressing the second strip touch sensor means at a contralateral cranial landmark;

measuring, by the second touch sensor means, the distance from the end of the second strip arrangement held to the lateral cranial landmark to the contralateral cranial landmark;

determining, by the control module, at least one location along the second strip arrangement for electrode placement, based on the measured distance and the electrode placement scheme; and illuminating the second flexible LED strip at determined location for guiding electrode placement.

15. The method according to claim 14 wherein placing the second strip arrangement over the head of the patient comprises placing the second strip arrangement along a line covering the Tragus landmarks; and wherein pressing the second strip arrangement at a contralateral cranial landmark comprises pressing the second strip arrangement at Tragus point.

16. The method according to claim 13 wherein placing the first strip arrangement over the head of the patient comprises placing the first strip arrangement along a line covering Inion and Nasion of the head; and wherein pressing the first strip arrangement on the section at a second cranial landmark comprises pressing the first strip arrangement at Inion point.

17. The method according to claim 13 further comprising an initial step of placing one strip arrangement along a line covering both Tragus for obtaining a central head reference point by the control module, wherein the obtained central head reference point guides the subsequent placement of the same or other strip arrangement along the line covering Inion and Nasion.

18. The method according to claim 13 further comprising illuminating each location determined for electrode placement of the LED strips with different colors and brightness based on the electrode placement scheme previously set; and wherein a location for electrode placement is located between two LEDs of any flexible LED strip, further comprising illuminating the nearest LED to the location with higher brightness and the furthest LED with lower brightness.

19. The method according to claim 13 further comprising matching, by the control module, one location of the electrode placement scheme previously set with a specific point on the scalp; and illuminating the first or the second flexible LED strip at the one location matched with the specific point.

* * * * *